(12) United States Patent
El Semary

(10) Patent No.: US 11,845,971 B1
(45) Date of Patent: Dec. 19, 2023

(54) GENERATION OF METHANE FROM DIGESTION OF MARINE BROWN ALGAE

(71) Applicant: KING FAISAL UNIVERSITY, Al-Ahsa (SA)

(72) Inventor: Nermin Adel El Semary, Al-Ahsa (SA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 18/143,529

(22) Filed: May 4, 2023

(51) Int. Cl.
| | | |
|---|---|---|
| *C12P 5/02* | (2006.01) | |
| *C12N 1/12* | (2006.01) | |
| *C12N 1/20* | (2006.01) | |
| C12R 1/38 | (2006.01) | |
| C12R 1/89 | (2006.01) | |
| C12R 1/44 | (2006.01) | |

(52) U.S. Cl.
CPC .............. *C12P 5/023* (2013.01); *C12N 1/125* (2021.05); *C12N 1/205* (2021.05); *C12R 2001/38* (2021.05); *C12R 2001/44* (2021.05); *C12R 2001/89* (2021.05)

(58) Field of Classification Search
CPC ......... C12P 5/023; C12N 1/125; C12N 1/205; C12R 2001/38; C12R 2001/44; C12R 2001/89
See application file for complete search history.

(56) References Cited

U.S. PATENT DOCUMENTS

| | | |
|---|---|---|
| 2013/0247451 A1 | 9/2013 | Vanhercke et al. |
| 2014/0273098 A1* | 9/2014 | Suryanarayan ......... C12P 19/00 435/72 |
| 2016/0002566 A1 | 1/2016 | Vanhercke et al. |
| 2018/0305656 A1 | 10/2018 | Wendt et al. |

OTHER PUBLICATIONS

Miura et al. "Improved methane production from brown algae under high salinity by fed-batch acclimation", Bioresource Technology, 2015;187:275-281; doi: 10.1016/j.biortech.2015.03.142; Epub Apr. 2, 2015. (Year: 2015).*
Soe-Hutn et al., "Checklist, distribution and potential utilization of marine algae of Myanmar I: *Chlorophyta* (green algae) and *Phaeophyta* (brown algae)", Jour. Myan. Acad. Arts & Sc 7.5 (2009): 2 (Year: 2009).*
https://en.wikipedia.org/wiki/Fusobacterium (Year: 2023).*
Soboh, "Anaerobic Co-Digestion of Algal Biomass and a Supplemental Carbon Source Material to Produce Methane", Utah State University, May 2015.
Milledge et al., "A Brief Review of Anaerobic Digestion of Algae for Bioenergy", Energies 2019, 12(6), 1166.
Fasahati et al., "Potential of brown algae for sustainable electricity production through anaerobic digestion", Energy Conversion and Management, vol. 135, Mar. 1, 2017, pp. 297-307.
Miura et al., "Improved methane production from brown algae under high salinity by fed-batch acclimation", Bioresource Technology, vol. 187, Jul. 2015, pp. 275-281.

* cited by examiner

*Primary Examiner* — Ruth A Davis
(74) *Attorney, Agent, or Firm* — Nath, Goldberg & Meyer; Richard C. Litman

(57) ABSTRACT

Methods for producing methane from algae, and particularly methods for producing methane from brown algae. The present methods can use a biomass of brown algae such as *Hormophysa cuneiformis* subjected to bacterial treatment to produce methane. The bacteria can comprise *Aeromonas sobria* and *Staphylococcus haemolyticus*. The brown algae and bacteria can all be obtained from the Arabian Gulf.

7 Claims, No Drawings

GENERATION OF METHANE FROM DIGESTION OF MARINE BROWN ALGAE

BACKGROUND

1. FIELD

The disclosure of the present patent application relates to methods for producing methane from algae, and particularly to methods for producing methane from brown algae.

2. DESCRIPTION OF THE RELATED ART

The increasing demand of fuel leading to fuel shortages along with increased energy costs and environmental concerns have created a need for alternative energy sources, particularly those that are renewable. Biofuels have become a popular alternative fuel source because they are renewable.

As the demand for biofuel and renewable industrial chemicals grows, so does the demand for biomass. At very large scales of operation, the consolidation and transportation of large volumes of low-density biomass overland is expensive and consumes a significant part of the energy generated. Biomass is typically grown on arable land, using large amounts of freshwater for irrigation and fertilizer. At a certain scale therefore, the demand for biomass for energy and industrial use begins to compete with agriculture for the purpose of food production, leading to unacceptable stresses in the food supply chain with a consequent escalation of food prices. In addition, the processing of biomass to biofuel and renewable chemicals at very large scales also involves the use of extremely large quantities of fresh water for hydrolyzing the biomass as well as for fermentation. Given the increasing shortage of freshwater resources, this represents a scalability issue. Furthermore, any such industrial process results in the formation of large quantities of waste streams which need to be treated and disposed of in an environmentally acceptable manner. All these issues could be prohibitive barriers in implementing such biomass-based processes widely and on a large scale.

Biomass produced from traditional agriculture or forestry operations has been the main source of fermentable sugars to produce a variety of useful products including renewable industrial chemicals and biofuel. The process of converting any kind of terrestrial biomass to such products generally involves collection and transportation of the biomass to a central processing location, pre-treatment of the biomass to make it amenable to further conversion, optionally followed by a treatment to break down the carbohydrate component of this biomass to fermentable sugars, followed by fermentation of these sugars with an appropriate strain of microorganism to produce the renewable industrial chemical or biofuel of interest.

Crops such as corn have been considered for producing biofuels because they are capable of being converted to alcohol. When ethanol is made from corn, it arguably takes more energy to produce the ethanol than is obtained from it. Also, using a grain such as corn for fuel precludes it from being used as food for humans. Corn production is also hard on the land because it erodes the soil. However, a biomass such as algae is capable of creating a fuel with a high power density, is renewable and, unlike corn, does not take away a food source from humans and livestock. The alternative to terrestrially grown biomass is to use aquatic photosynthetic biomass such as seaweed or algae that can be easily grown in a saltwater environment, without using freshwater and fertilizers.

The energy in biomass can be accessed by turning the raw materials, or feedstocks, into a usable form. Transportation fuels made from biomass through biochemical or thermochemical processes are known as biofuels which include ethanol, methanol, biodiesel, biocrude, and methane.

Methane is the major component of compressed natural gas, an alternative transportation fuel. Methane, in a blend of other gases, can typically be produced from biomass by a biochemical process called anaerobic digestion.

Most of the processes for production of seaweed or algal biomass known in the prior art describe removal of salt before further processing. Further, freshwater and/or fertilizer have been used in the cultivation of seaweed and further processing of seaweed for producing useful chemicals and biofuel. Further, the downstream process involved in using seawater-based biomass, starting with drying and transportation followed by hydrolysis and fermentation, are carried out in a conventional manner, using freshwater that is not different from the way land based agricultural biomass is treated. Such processes at a large scale, using large amounts of fresh water and generating correspondingly large amounts of waste to be disposed of, are not scalable and sustainable.

Thus, cost effective, easy, sustainable, and less time-consuming processes for production of biofuels from seaweed or algal biomass solving the aforementioned problems are desired.

SUMMARY

The present subject matter relates to new methods for producing methane from algae, and particularly to methods for producing methane from brown algae.

In one embodiment, the present subject matter relates to a process for producing methane from brown algae, the process comprising: providing a biomass consisting essentially of brown algae; subjecting the biomass of brown algae to bacterial treatment to produce methane; and recovering the methane.

In another embodiment, the present subject matter relates to a process for producing methane from *Hormophysa cuneiformis* brown algae, the process comprising: providing a biomass consisting essentially of *Hormophysa cuneiformis* brown algae; subjecting the biomass of brown algae to bacteria isolated from decomposing mass of the *Hormophysa cuneiformis* brown algae, wherein the bacteria comprise *Aeromonas sobria* and *Staphylococcus haemolyticus* to produce methane; and recovering the methane.

In a further embodiment, the present subject matter relates to a process for producing methane from *Hormophysa cuneiformis* brown algae, the process comprising: providing a biomass consisting essentially of *Hormophysa cuneiformis* brown algae; subjecting the biomass of brown algae to bacteria isolated from decomposing mass of the *Hormophysa cuneiformis* brown algae, wherein the bacteria comprise *Aeromonas sobria* and *Staphylococcus haemolyticus;* fermenting the biomass of *Hormophysa cuneiformis* brown algae with the bacteria to obtain fermentation products; producing acetic acid from the biomass of *Hormophysa cuneiformis* brown algae with the bacteria; initiating anaerobic digestion of the biomass of *Hormophysa cuneiformis* brown algae using the fermentation products and the acetic acid to produce methane; and recovering the methane.

These and other features of the present subject matter will become readily apparent upon further review of the following specification.

DETAILED DESCRIPTION OF THE PREFERRED EMBODIMENTS

The following definitions are provided for the purpose of understanding the present subject matter and for construing the appended patent claims.

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

The term "optional" or "optionally" means that the subsequently described event or circumstance may or may not occur, and that the description includes instances where said event or circumstance occurs and instances in which it does not.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

The present subject matter relates to new methods for producing methane from algae, and particularly to methods for producing methane from brown algae.

In one embodiment, the present subject matter relates to a process for producing methane from brown algae, the process comprising: providing a biomass consisting essentially of brown algae; subjecting the biomass of brown algae to bacterial treatment to produce methane; and recovering the methane. In certain alternative embodiments, the biomass can comprise or can consist of the brown algae.

In one embodiment, the brown algae used in the present process can be *Hormophysa cuneiformis*. Other suitable brown algae may further be useful herein.

In another embodiment, the bacterial treatment comprises the use of bacteria isolated from decomposing mass of the brown algae, such as the *Hormophysa cunieformis* brown algae. In this regard, the bacteria isolated from the decomposing mass of the *Hormophysa cunieformis* brown algae can comprise *Aeromonas sobria* and *Staphylococcus haemolyticus*. These bacteria, most notably the *Aeromonas sobria*, can typically be found in aquatic habitats. It is expected that the decomposing mass of other brown algae will comprise these same bacteria. In any event, the biomass of *Hormophysa cunieformis* brown algae and the bacteria are both native to and can both be isolated and obtained from the Arabian Gulf. The presence and isolation of *Hormophysa cunieformis* brown algae and the *Aeromonas sobria* and *Staphylococcus haemolyticus* bacteria from the Arabian Gulf have never been previously reported.

In certain embodiments, the present processes for preparing methane can further comprise fermenting the biomass of brown algae with the *Aeromonas sobria* and *Staphylococcus haemolyticus* bacteria to obtain fermentation products and/or producing acetic acid from the biomass of brown algae with the *Aeromonas sobria* and *Staphylococcus haemolyticus* bacteria. One or both such bacteria can be used to initiate, and can be present during, the methane production process. In this regard, the fermentation products and the acetic acid can be used to initiate anaerobic digestion of the remaining biomass of brown algae and, therefore, the production of methane. Notably, this process will be conducted as an anaerobic process. These processes mimic those found in nature, where large masses of algae can induce anaerobic conditions that initiate methane production. Further, the *Aeromonas sobria* and *Staphylococcus haemolyticus* bacteria specifically contribute to the digestion of the *Hormophysa cunieformis* brown algae. The resultant methane production was confirmed via gas chromatography.

As stated herein, the production of methane is in vivo production from the decomposition of the *Hormophysa* cunieformis brown algae by the *Aeromonas sobria* and *Staphylococcus haemolyticus* bacteria. The methane as produced herein can be further used as a biofuel, or can otherwise be used for energy generation on a small or large scale.

Accordingly, in another embodiment, the present subject matter relates to a process for producing methane from *Hormophysa cuneiformis* brown algae, the process comprising: providing a biomass consisting essentially of *Hormophysa cuneiformis* brown algae; subjecting the biomass of brown algae to bacteria isolated from decomposing mass of the *Hormophysa cuniefomis* brown algae, wherein the bacteria comprise *Aeromonas sobria* and *Staphylococcus haemolyticus* to produce methane; and recovering the methane.

In a further embodiment, the present subject matter relates to a process for producing methane from *Hormophysa cuneiformis* brown algae, the process comprising: providing a biomass consisting essentially of *Hormophysa cuneiformis* brown algae; subjecting the biomass of brown algae to bacteria isolated from decomposing mass of the *Hormophysa cuneiformis* brown algae, wherein the bacteria comprise *Aeromonas sobria* and *Staphylococcus haemolyticus*; fermenting the biomass of *Hormophysa cuneiformis* brown algae with the bacteria to obtain fermentation products; producing acetic acid from the biomass of *Hormophysa cuneiformis* brown algae with the bacteria; initiating anaerobic digestion of the biomass of *Hormophysa cuneiformis* brown algae using the fermentation products and the acetic acid to produce methane; and recovering the methane.

These and other features of the present subject matter can be further considered by referring to the following examples.

EXAMPLES

Example 1

The following laboratory results in the following Tables 1-4 demonstrate that the *Aeromonas sobria* and *Staphylococcus haemolyticus* digesting bacteria were identified as specifically being present, and thus being obtained from, the Arabian Gulf.

*Aeromonas Sobria*

TABLE 1

| Identification Information | Card: | GN | Lot Number: | 2412046503 | Expires: | Jul. 4, 2023 13:00 CDT |
|---|---|---|---|---|---|---|
| | Completed: | Nov. 17, 2022 18:29 CST | Status: | Final | Analysis Time: | 9.93 hours |
| Organism Orgin | VITEK 2 | | | | | |
| Selected Organism | 85% Probability | | *Aeromonas sobria* | | | |
| | Bionumber: | 4021200050140210 | | | Confidence: | Acceptable idenification |
| SRF Organism | | | | | | |
| Analysis Organism and Tests to Separate: | | | | | | |
| Analysis Message: | | | | | | |
| Contraindicating Typical Biopattern(s) | | | | | | |

*Aeromonas sobria* dMNE(99), ELLM(96), ProA(99).

TABLE 2

| Biochemical Details | | | | | | | | | | | |
|---|---|---|---|---|---|---|---|---|---|---|---|
| 2 APPA | − | 3 ADO | − | 4 PyrA | + | 5 IARL | − | 7 dCEL | − | 9 BGAL | − |
| 10 H2S | (−) | 11 BNAG | + | 12 AGLTp | − | 13 dGLU | + | 14 GGT | − | 15 OFF | − |
| 17 BGLU | − | 18 dMAL | + | 19 dMAN | − | 20 dMNE | − | 21 BXYL | − | 22 BAlap | − |
| 23 ProA | − | 26 LIP | − | 27 PLE | − | 29 TyrA | − | 31 URE | − | 32 dSOR | − |
| 33 SAC | + | 34 dTAG | − | 35 dTRE | + | 36 CIT | − | 37 MNT | − | 39 5KG | − |
| 40 ILATk | + | 41 AGLU | − | 42 SUCT | − | 43 NAGA | − | 44 AGAL | − | 45 PHOS | (+) |
| 46 GlyA | − | 47 ODC | − | 48 LDC | − | 53 IHISa | − | 56 CMT | + | 57 BGUR | − |
| 58 O129R | + | 59 GGAA | − | 61 IMLTa | − | 62 ELLM | − | 64 ILATa | − | | |

*Staphylococcus Haemolyticus*

TABLE 3

| Identification Information | Card: | GP | Lot Number: | 2422088503 | Expires: | Aug. 15, 2023 13:00 CDT |
|---|---|---|---|---|---|---|
| | Completed: | Nov. 17, 2022 14:20 CST | Status: | Final | Analysis Time: | 5.78 hours |
| Organism Orgin | VITEK 2 | | | | | |
| Selected Organism | 95% Probability | | *Straphylococcus haemolyticus* | | | |
| | Bionumber: | 010402021720231 | | | Confidence: | Very good idenification |

TABLE 3-continued

SRF
Organism
Analysis Organism and Tests to Separate:
Analysis Message:
Contraindicating Typical Biopattern(s)

*Straphylococcus haemolyticus*   POLYB(1).

TABLE 4

Biochemical Details

| 2 AMY | − | 4 PIPLC | − | 5 dXYL | − | 8 ADH1 | + | 9 BGAL | − | 11 AGLU | − |
|---|---|---|---|---|---|---|---|---|---|---|---|
| 13 APPA | − | 14 CDEX | − | 15 AspA | − | 16 BGAR | − | 17 AMAN | − | 19 PHOS | (+) |
| 20 LeuA | − | 23 ProA | − | 24 BGURr | − | 25 AGAL | − | 26 PyrA | + | 27 BGUR | − |
| 28 AlaA | − | 29 TyrA | − | 30 dSOR | − | 31 URE | − | 32 POLYB | + | 37 dGAL | − |
| 38 dRIB | − | 39 ILATk | − | 42 LAC | − | 44 NAG | + | 45 dMAL | + | 46 BACl | + |
| 47 NOVO | − | 50 NC6.5 | + | 52 dMAN | − | 53 dMNE | − | 54 MBdG | − | 56 PUL | − |
| 57 dRAF | (−) | 58 O129R | + | 59 SAL | − | 60 SAC | + | 62 dTRE | + | 63 ADH2s | − |
| 64 OPTO | + | | | | | | | | | | |

It is to be understood that the process described herein is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A process for producing methane from brown algae, the process comprising:
providing a biomass consisting essentially of brown algae, the brown algae being *Hormophysa cuneiformis;*
contacting the biomass with bacteria isolated from decomposing mass of the *Hormophysa cuneiformis* brown algae to produce methane, the bacteria comprising *Aeromonas sobria* and *Staphylococcus haemolyticus;* and
recovering the methane.

2. The process as recited in claim 1, wherein the biomass of *Hormophysa cuneiformis* brown algae and the bacteria are obtained from the Arabian Gulf.

3. The process as recited in claim 1, further comprising fermenting the biomass of brown algae with the bacteria to obtain fermentation products.

4. The process as recited in claim 3, wherein the fermentation products comprise acetic acid.

5. The process as recited in claim 4, wherein the fermentation products and the acetic acid initiate anaerobic digestion of the biomass of brown algae and the production of methane.

6. The process as recited in claim 1, wherein the process is an anaerobic process.

7. A process for producing methane from *Hormophysa cuneiformis* brown algae, the process comprising:
providing a biomass consisting essentially of *Hormophysa cuneiformis* brown algae;
contacting the biomass with bacteria isolated from decomposing mass of the *Hormophysa cuneiformis* brown algae, wherein the bacteria comprise *Aeromonas sobria* and *Staphylococcus haemolyticus;*
fermenting the biomass of *Hormophysa cuneiformis* brown algae with the bacteria to obtain fermentation products, the fermentation products including acetic acid;
initiating anaerobic digestion of the biomass of *Hormophysa cuneiformis* brown algae using the fermentation products and the acetic acid to produce methane; and
recovering the methane.

* * * * *